US00PP19701P2

(12) United States Plant Patent
Schmulling

(10) Patent No.: US PP19,701 P2
(45) Date of Patent: Feb. 10, 2009

(54) ***OSTEOSPERMUM* PLANT NAMED 'DEL COM BW'**

(50) Latin Name: *Osteospermum ecklonis*
Varietal Denomination: DEL COM BW

(76) Inventor: Markus Schmulling, Temming 83, Billerbeck (DE), 48727

( * ) Notice: Subject to any disclaimer, the term of this patent is extended or adjusted under 35 U.S.C. 154(b) by 27 days.

(21) Appl. No.: 11/824,109

(22) Filed: Jun. 30, 2007

(51) Int. Cl.
*A01H 5/00* (2006.01)

(52) U.S. Cl. ..... Plt./360
(58) Field of Classification Search ..... Plt./360
See application file for complete search history.

*Primary Examiner*—Kent L Bell

(57) ABSTRACT

A new and distinct *Osteospermum* plant cultivar is disclosed, characterized by small spoon daisy type inflorescences, freely flowering, compact growth habit, magenta inflorescences with a dark purple and violet underside and a dark purple center, and a high heat tolerance.

1 Drawing Sheet

Latin name of the genus and species: *Osteospermum ecklonis*.
Variety denomination: 'DEL COM BW'.

BACKGROUND OF THE INVENTION

The new cultivar 'DEL COM BW' is a product of open pollination in a heterogeneous population of *Osteospermum* mass selection in 2004. The exact parents are unknown even though 'DEL COM BW' is a product of open pollination. The new cultivar was discovered and selected by Markus Schmulling in June 2005 in Billerbeck, Germany.

Asexual reproduction of the new cultivar 'DEL COM BW' by cuttings from adventitious shoots was performed in Oxnard, Calif., and has shown that the unique features of this new cultivar are stable and reproduced true to type on successive generations.

SUMMARY OF THE INVENTION

The cultivar 'DEL COM BW' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'DEL COM BW.' These characteristics in combination distinguish 'DEL COM BW' as a new and distinct *Osteospermum* cultivar:

1. Small spoon daisy type inflorescence;
2. Freely flowering, compact growth habit;
3. Magenta inflorescences with a dark purple and violet underside and a dark purple center; and
4. A high heat tolerance.

Plants of the new cultivar differ from plants of the parent selections in growth habit and size, inflorescence size and level of heat tolerance.

In comparison to the commercially available variety 'Balserlabli' (U.S. Plant Pat. No. 16,509), 'DEL COM BW' has a more compact growth habit with more inflorescences per lateral branch. Additionally, 'DEL COM BW' has a smaller inflorescence diameter. Finally, the ray florets of 'DEL COM BW' are a more red-purple in color and the disc florets are dark purple compared to the lighter violet-blue disc florets of the comparable variety.

BRIEF DESCRIPTION OF THE PHOTOGRAPH

The accompanying photograph in FIG. 1 illustrates in full color a typical plant of 'DEL COM BW' grown in an outdoor garden. The growing temperature ranged from 12° C. to 15° C. at night to 12° C. to 20° C. during the day. The colors are as nearly true as is reasonably possible in a color representation of this type.

DETAILED BOTANICAL DESCRIPTION

In the following description, color references are made to the Royal Horticultural Society Colour Chart except where general terms of ordinary dictionary significance are used. The following observations and measurements describe 'DEL COM BW' plants grown in Oxnard, Ventura County, Calif., during the months of January through June in an outdoor garden. The growing temperature ranged from 12° C. to 15° C. at night to 12° C. to 20° C. during the day. Measurements and numerical values represent averages of typical flowering types.

Botanical classification: *Osteospermum ecklonis* cultivar 'DEL COM BW.'
Commercial classification: Garden-type *Osteospermum*.

PROPAGATION

Time to rooting: 10 to 14 days at approximately 22° C.
Root description: Fine, fibrous.

PLANT

Growth habit: Mounding outwardly spreading herbaceous perennial.
Height: Approximately 36 cm.
Plant spread: Approximately 87 cm.
Growth rate: Medium.
Branching characteristics: Free Branching.
Length of lateral branches: Approximately 29 cm.
Number of leaves per lateral branch: Approximately 98.
Age of plant described: Approximately 137 days.

FOLIAGE

Leaf:
*Arrangement.*Alternate single.
*Average length.*—Approximately 4.2 cm.
*Average width.*—Approximately 1.8 cm.
*Shape of blade.*—Obovate.
*Apex.*—Abruptly acuminate.
*Base.*—Attenuate.
*Attachment.*—Stalked.
*Margin.*—Entire with occasional tiny serrations.
*Texture of top surface.*—Lightly pubescent.
*Texture of bottom surface.*—Lightly pubescent.
*Leaf internode length.*—Approximately 1.6 cm.
*Color.*—Young foliage upper side: Near Green 137A. Young foliage under side: Near Green 137C. Mature foliage upper side: Near Green 137A. Mature foliage under side: Near Green 137C.
*Venation.*—Type: Pinnate. Venation color upper side: Near Green 143C. Venation color under side: Near Green 143C.

Petiole:
*Average length.*—Approximately 1.2 cm.
*Color.*—Near Green 143C.
*Diameter.*—Approximately 0.3 cm.

BLOOM

Inflorescence:
*Flowering habit.*—Freely flowering under outdoor growing conditions with continuous blooming from spring through autumn and year round in a greenhouse environment.
*Inflorescence form.*—Spoon daisy.
*Natural flowering season.*—Continuous throughout February to September in temperate regions.
*Number of inflorescences per lateral branch.*—Approximately 12.
*Inflorescence diameter.*—Approximately 4.7 cm.
*Inflorescence depth.*—Approximately 1.6 cm.
*Disc diameter.*—Approximately 1.1 cm.
*Inflorescence longevity on plant.*—Approximately 6 to 10 days; longevity of individual flowers are very dependent on temperature and light conditions.
*Persistence.*—Persistent.

Ray Florets:
*Appearance.*—Matte on upper surface, shiny on under surface.
*Texture.*—Smooth.
*Average number of ray florets per inflorescence.*—20 in one or two whorls.
*Shape.*—Oblanceolate.
*Aspect.*—Slightly cupped, facing upward or outward.
*Margin.*—Entire.
*Apex.*—Obtuse.
*Average length.*—Approximately 2.1 cm.
*Average width.*—Approximately 0.4 cm.
*Color.*—Upper surface at first opening: Near Red-Purple 72B. Upper surface at maturity: Near Red-Purple 72A. Upper surface at fading: Near Purple 77D. Under surface at first opening: Near Purple 79A with streaks of Purple 77B. Under surface at maturity: Near Purple 79A with streaks of Purple 77B. Under surface at fading: Near Purple 79A with streaks of Purple 77B.

Disc Florets:
*Appearance.*—Shiny.
*Texture.*—Smooth.
*Average number of florets per disc.*—Approximately 64.
*Shape.*—Tubular.
*Apex.*—Five-pointed.
*Average length.*—Approximately 0.4 cm.
*Average width.*—Approximately 0.15 cm.
*Color.*—At first opening: Near Purple 79A. At maturity: Near Purple 79A. At fading: Near Purple 79A.

Peduncle:
*Length.*—Between 8 and 18 cm.
*Angle.*—Terminal peduncles, erect; secondary and tertiary peduncles, about 45° from vertical.
*Strength.*—Moderate.
*Color.*—Near Yellow-Green 144B.
*Habit.*—Upright.
*Diameter.*—Approximately 0.2 cm.
*Surface texture.*—Lightly pubescent.

Inflorescence bud:
*Length.*—Approximately 0.5 cm.
*Diameter.*—Approximately 0.4 cm.
*Form.*—Elliptic.
*Color.*—Near Green 138A.

Involucral bracts (phyllaries):
*Appearance.*—Matte.
*Texture.*—Lightly pubescent.
*Number.*—Approximately 18.
*Shape.*—Lanceolate.
*Margin.*—Entire.
*Apex.*—Narrowly acute.
*Length.*—Approximately 0.9 cm.
*Width.*—Approximately 0.3 cm.
*Color.*—Upper side: Near Yellow-Green 144B. Underside: Near Yellow-Green 144B.

REPRODUCTIVE ORGANS

Androecium: Present on disc florets only.
*Number of stamens.*—5.
*Anther shape.*—Linear.
*Anther length.*—Approximately 1.2 mm.
*Anther color.*—Near Purple 79A.
*Amount of pollen.*—Minimal.
*Pollen color.*—Near Yellow-Orange 14A.

Gynoecium: Present on ray and disc florets.
*Pistil number.*—One.
*Pistil length.*—Approximately 3 mm.
*Stigma shape.*—Two parted.
*Stigma length.*—Approximately 1.1 mm.
*Stigma color.*—Near Purple 79A.
*Style length.*—Approximately 1.15 mm.
*Style color.*—Near Purple 77A.

OTHER CHARACTERISTICS

Disease resistance: Neither resistance nor susceptibility to diseases or pests has been observed in this variety.

Drought tolerance/cold tolerance: Plants are moderately drought tolerant. Plants need cold, less than 12.8° C. for flower induction.

Fruit/Seed production: Commercially, this plant is not used or observed in a stage where seeds would be produced. Therefore, seed production has not been observed.

What is claimed is:

1. A new and distinct cultivar of *Osteospermum* plant named 'DEL COM BW' as herein illustrated and described.

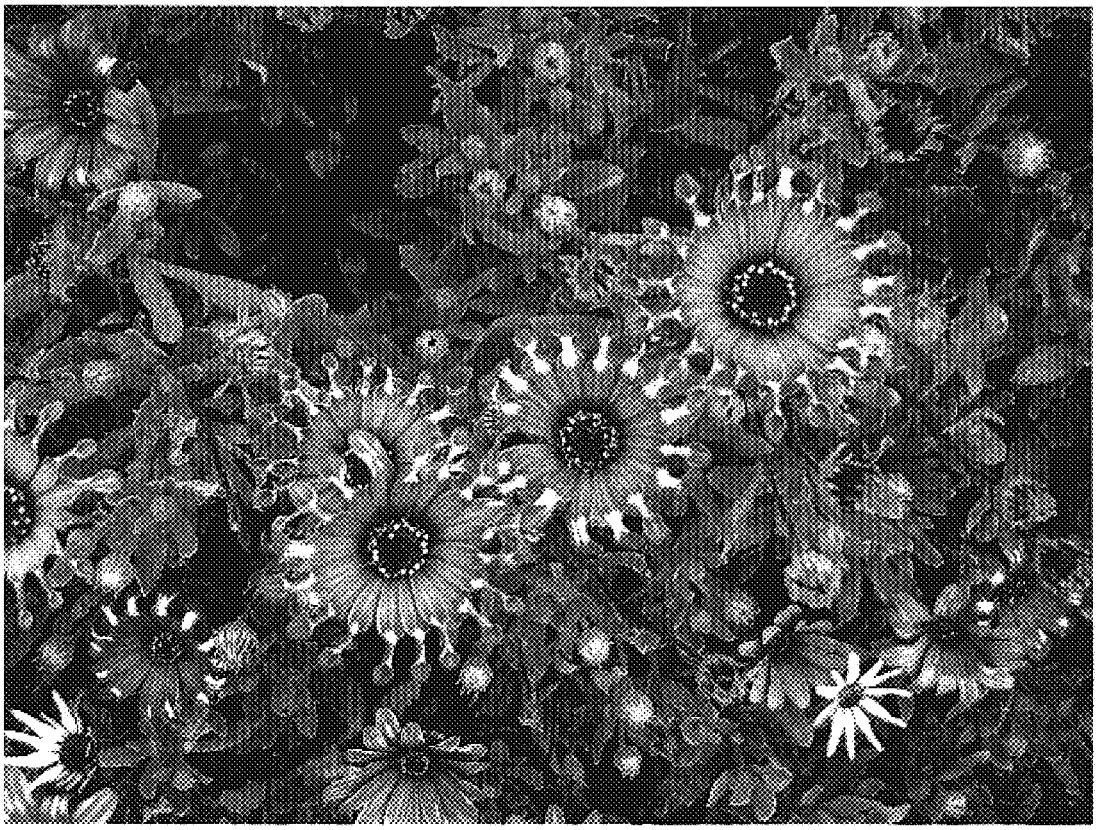

* * * * *